United States Patent [19]

Isobe et al.

[11] Patent Number: 5,693,605
[45] Date of Patent: Dec. 2, 1997

[54] DETERGENT COMPOSITION COMPRISING AN AMIDE-ETHER DERIVATIVE MIXTURE AND AN ANIONIC SURFACTANT

[75] Inventors: Kazuo Isobe; Toshikazu Azuma, both of Wakayama; Hideyo Nishikawa, Funabashi; Takashi Imamura, Hannan, all of Japan

[73] Assignee: Kao Corporation, Tokyo, Japan

[21] Appl. No.: 624,632

[22] Filed: Apr. 10, 1996

[30] Foreign Application Priority Data

Aug. 10, 1994 [JP] Japan .................. 6-188060

[51] Int. Cl.⁶ .................. C11D 1/12; C11D 1/66; C11D 3/32

[52] U.S. Cl. .................. 510/499; 510/126; 510/501; 510/502; 510/235; 510/237; 510/119; 510/123; 510/135; 510/503; 550/124; 550/130; 550/137; 514/852

[58] Field of Search .................. 510/126, 501, 510/502, 235, 237, 119, 123, 135, 503; 550/124, 130, 137; 514/852

[56] References Cited

U.S. PATENT DOCUMENTS

| | | | |
|---|---|---|---|
| 4,783,282 | 11/1988 | Smid | 252/546 |
| 4,818,440 | 4/1989 | Schafer et al. | 252/546 |
| 4,865,757 | 9/1989 | Singh-Verma et al. | 252/117 |
| 5,478,490 | 12/1995 | Russo et al. | 252/153 |

FOREIGN PATENT DOCUMENTS

| | | |
|---|---|---|
| 327-490-0 | 8/1995 | WIPO . |
| 327-548-0 | 4/1996 | WIPO . |

*Primary Examiner*—Paul Lieberman
*Assistant Examiner*—Charles Boyer
*Attorney, Agent, or Firm*—Oblon, Spivak, McClelland, Maier & Neustadt, P.C.

[57] ABSTRACT

A detergent composition, comprising (A) an amide-ether derivative mixture comprising an amide-ether carboxylic acid or a salt thereof (1) and an amide-ether (2) in a weight ratio (1)/(2) of 99:1 to 10:90 in a proportion of at least 50 wt. % in total based on solids in the component (A), and containing glycerol derivatives (3) in a proportion not higher than 5 wt. % of the solids, and (B) a specific anionic surfactant such as a polyoxyalkylene alkyl ether sulfosuccinate (salt) or α-olefinsulfonic acid (salt).

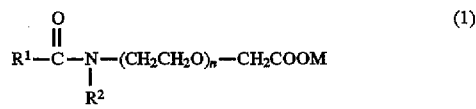

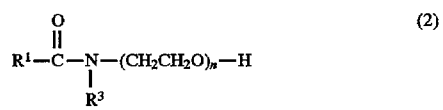

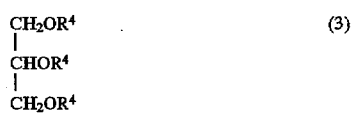

wherein $R^1$ is a $C_{5\text{-}23}$ alkyl or alkenyl group, or a phenyl group substituted by such an alkyl group, $R^2$ is H, $-(CH_2CH_2O)_nCH_2COOM$, $-(CH_2CH_2O)_mH$ or $C_{1\text{-}3}$ alkyl group, M is a cation such as H or alkali metal, n and m are independently a number of 1–20, $R^3$ is H, $-(CH_2CH_2O)_mH$ or $C_{1\text{-}3}$ alkyl group, and $R^4$ is H, $-(CH_2CH_2O)_nCH_2COOM$ or $-(CH_2CH_2O)_mH$.

The composition has low irritativeness and high foamability, and produce creamy foams.

5 Claims, No Drawings

DETERGENT COMPOSITION COMPRISING AN AMIDE-ETHER DERIVATIVE MIXTURE AND AN ANIONIC SURFACTANT

TECHNICAL FIELD

The present invention relates to a detergent composition, and particularly to a detergent composition which has low irritativeness to the skin and the like and excellent foamability, and produces creamy foams.

BACKGROUND ART

Anionic surfactants such as alkylsulfates, polyoxyethylene alkylsulfates, alkylbenzenesulfonates and α-olefinsulfonates, which have the merit of high foamability, have heretofore been used widely as surfactants for detergents. However, all these surfactants involve a problem that they more or less have irritativeness to the skin and roughen the skin during repeated use.

On the other hand, alkylsaccharide type surfactants, sulfosuccinic acid type surfactants, ether carboxylic acid type surfactants, amide-ether carboxylic acid type surfactants, etc. have been known as low-irritative surfactants. However, the alkylsaccharide type surfactants have high foamability, but give a strong creaky feel upon washing and rinsing. Therefore, it is technically difficult to incorporate them in a large amount in shampoos and the like though a method of using them in combination with a conditioning agent such as a cationic polymer (Japanese Patent Application Laid-Open No. 42013/1990), and the like have been proposed. The sulfosuccinic acid type surfactants per se are poor in foamability, and a method of using them in combination with other surfactants (Japanese Patent Application Laid-Open No. 218797/1990), and the like have been proposed. They are often practically used in combination with other surfactants. Commercially-available ether carboxylic acid type surfactants and amide-ether carboxylic acid type surfactants are also poor in foamability and hence used only as co-surfactants in detergents of which high foamability is required.

Amide-ether carboxylic acid type surfactants are commercially-available from Chem-Y GmbH in Germany under the trade name of "Akypo". These products contain an amide-ether carboxylic acid and an amide-ether, which is a raw material therefor, and besides, polyoxyethylene glyceryl ether, polyoxyethylene glyceryl ether carboxylic acid, inorganic salts and the like, which are impurities derived from raw materials.

Techniques as to the application of the amide-ether carboxylic acid type surfactants to detergents, which have been known to date, include a cosmetic composition comprising an amide-ether carboxylic acid (European Patent No. 102118), a detergent composition comprising an amide-ether carboxylic acid type surfactant and a polyoxyethylene alkylsulfate in combination (European Patent No. 215504), an amide-ether carboxylic acid produced by using, as a starting material, oil and fat, and a detergent containing the same (Japanese Patent Application Laid-Open No. 291996/1988, European Patent No. 219893), and a detergent comprising soap, as a main component, and an amide-ether carboxylic acid, an alkyl ether carboxylic acid or salt thereof (U.S. Pat. No. 4,865,757).

However, none of these detergents have been yet satisfactory from the viewpoint of foamability. There have thus been demand for development of a detergent which has low irritativeness to the skin and the like and high foamability.

In view of the foregoing circumstances, the present inventors have carried out an investigation as to detergents containing an amide-ether carboxylic acid. As a result, it has been found that detergents containing polyoxyethylene glyceryl ether and polyoxyethylene glyceryl ether carboxylic acid, which are impurities derived from a raw material, in a large amount, or a pure amide-ether carboxylic acid itself are poor in foamability. A further investigation has revealed that when an amide-ether derivative mixture comprising an amide-ether in a specific proportion and containing glycerol derivatives in a amount not higher than a certain proportion is used in combination with a specific anionic surfactant, a detergent, which has low irritativeness to the skin and the like and high foamability, and produces creamy foams, can be provided, thus leading to completion of the present invention.

DISCLOSURE OF THE INVENTION

The present invention is directed to a detergent composition comprising the following components (A) and (B):

(A) an amide-ether derivative mixture comprising an amide-ether carboxylic acid or a salt thereof represented by the following general formula (1) and an amide-ether represented by the following general formula (2) in a weight ratio (1)/(2) of 99:1 to 1:9 in a proportion of at least 50 wt. % in total based on solids in the component (A), and containing glycerol derivatives represented by the following general formula (3) in a proportion not higher than 5 wt. % of the solids:

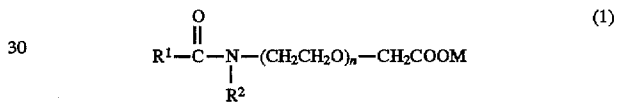

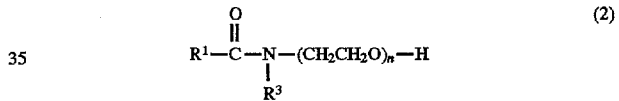

wherein $R^1$ is a linear or branched alkyl or alkenyl group having 5–23 carbon atoms, or a phenyl group substituted by such an alkyl group, $R^2$ is a hydrogen atom, $-(CH_2CH_2O)_nCH_2COOM$, $-(CH_2CH_2O)_mH$ or an alkyl group having 1–3 carbon atoms, M is a hydrogen atom, alkali metal, alkaline earth metal, ammonium, alkanolamine or basic amino acid, n and m may be identical with or different from each other and are independently a number of 1–20, $R^3$ is a hydrogen atom, $-(CH_2CH_2O)_mH$ or an alkyl group having 1–3 carbon atoms, and $R^4$ is a hydrogen atom, $-(CH_2CH_2O)_nCH_2COOM$ or $-(CH_2CH_2O)_mH$, with the proviso that respective $R^1$, M, n and m in the general formulae (1), (2) and (3) may be identical with or different from one another; and (B) an anionic surfactant selected from the group consisting of alkyl sulfosuccinates, polyoxyalkylene alkyl ether sulfosuccinates, polyoxyalkylene fatty acid amide ether sulfuric acids, monoglyceride sulfuric acids, α-olefinsulfonic acids, acylated isethionic acids, alkyl glyceryl ether sulfonic acids, acylated glutamic acids and alkanesulfonic acids, as well as salts thereof.

BEST MODE FOR CARRYING OUT THE INVENTION

In the amide-ether derivative mixture of the component (A) used in the present invention, $R^1$ in the general formula (1) or (2) is preferably an alkyl or alkenyl group having 7–17 carbon atoms, or a phenyl group substituted by such an alkyl group. For example, heptyl, nonyl, undecyl, dodecyl, tridecyl, pentadecyl, heptadecyl and heptadecenyl groups are more preferred. Alkyl groups having 11–13 carbon atoms are particularly preferred. $R^2$ is preferably a hydrogen atom or an alkyl group having 1–3 carbon atoms, and n and m independently are preferably a number of 1–15, more preferably 1–10, most preferably 2–7. Preferable examples of M include sodium, potassium, magnesium, calcium, monoethanolamine, diethanolamine, triethanolamine, arginine and lysine. Of these, sodium, potassium, magnesium and calcium are particularly preferred.

Although various compounds included in the general formula (1) may be exemplified as the amide-ether carboxylic acid or its salt (1) in the component (A), preferable specific examples thereof include lauric acid monoethanolamide polyoxyethylene ether acetic acid (n=1–10), myristic acid monoethanolamide polyoxyethylene ether acetic acid (n=1–10), palmitic acid monoethanolamide polyoxyethylene ether acetic acid (n=1–10) and stearic acid monoethanolamide polyoxyethylene ether acetic acid (n=1–10), or salts thereof. Particularly preferable specific examples thereof include lauric acid monoethanolamide polyoxyethylene ether acetic acid (n=2–7) and myristic acid monoethanolamide polyoxyethylene ether acetic acid (n=2–7).

Although various compounds included in the general formula (2) may be exemplified as the amide-ether (2) in the component (A), preferable specific examples thereof include lauric acid monoethanolamide polyoxyethylene ether (n=1–10), myristic acid monoethanolamide polyoxyethylene ether (n=1–10), palmitic acid monoethanolamide polyoxyethylene ether (n=1–10) and stearic acid monoethanolamide polyoxyethylene ether (n=1–10). Particularly preferable specific examples thereof include lauric acid monoethanolamide polyoxyethylene ether (n=2–7) and myristic acid monoethanolamide polyoxyethylene ether (n=2–7).

The total content of the amide-ether carboxylic acid or its salt (1) and the amide-ether (2) in the amide-ether derivative mixture of the component (A) is preferably 50–100 wt. % based on solids in the component (A). It is preferably at least 60 wt. %, more preferably at least 70 wt. %, most preferably at least 80 wt. %.

The weight ratio (1)/(2) between the amide-ether carboxylic acid or its salt (1) and the amide-ether (2) contained in the component (A) must be 99:1 to 10:90. It is preferably 95:5 to 60:40, most preferably 92:8 to 70:30. If the proportion of the amide-ether (2) is lower than the lower limit of this range (lower than 1 wt. %), the resulting detergent composition becomes deteriorated in foamability. On the other hand, any proportion exceeding the upper limit results in a detergent composition which gives a strong creaky feel upon foaming or rinsing. It is hence not preferable to add the amide-ether in any proportion outside the above range.

The content of the glycerol derivatives (3) in the component (A) is preferably not higher than 5 wt. %, more preferably not higher than 3 wt. % based on solids in the component (A). It is particularly preferred that the glycerol derivatives (3) be substantially not contained. If the content of the glycerol derivatives (3) exceeds 5 wt. % of the solids, the resulting detergent composition tends to be deteriorated in foamability. The content of inorganic salts such as sodium chloride, which are impurities other than the glycerol derivatives (3) in the component (A), is preferably as low as possible.

No particular limitation is imposed on the preparation method of the amide-ether derivative mixture, and it may be directly prepared by partially reacting an amide-ether to convert to its corresponding amide-ether carboxylic acid. Alternatively, the mixture may be prepared by adding an amide-ether to an amide-ether carboxylic acid. As examples of a process for synthesizing the amide-ether derivative mixture, may be mentioned a process in which a lower alcohol ester of a fatty acid, such as the methyl ester of a fatty acid, is used as a starting material to prepare an alkanolamide, a process in which oil and fat are used as a starting material to prepare an alkanolamide and a process in which a fatty acid is used as a starting material to prepare an alkanolamide. Of these, the preparation process in which a lower alcohol ester of a fatty acid, such as the methyl ester of a fatty acid, is used as a starting material is preferred because color development scarcely occurs, and the glycerol derivatives, which are impurities, are substantially not contained. In the case of another process, for example, a process in which oil and fat having a fatty acid composition of coconut oil are used as a starting material to directly prepare an alkanolamide, which is then subjected to alkoxylation and carboxymethylation, the glycerol derivatives derived from the oil and fat are formed in plenty, and so yields of the compounds (1) and (2) are reduced. Therefore, such a process is practically not preferred. The ratio between the amide-ether carboxylic acid (1) and the amide-ether (2) in the amide-ether derivative mixture of the component (A) can be controlled by selecting reaction conditions such as molar ratio of monohaloacetic acid alkali salt or the like with the amide-ether (2), or a mixing method thereof.

These components (A) may be used either singly or in any combination thereof. No particular limitation is imposed on the amount of the component (A) to be incorporated into the detergent composition according to the present invention. However, it is preferably incorporated in a proportion of at least 3 wt. %, more preferably 3–30 wt. %, most preferably 5–20 wt. % from the viewpoint of foamability.

The anionic surfactant of the component (B) useful in the practice of the present invention is selected from the group consisting of alkyl sulfosuccinates, polyoxyalkylene alkyl ether sulfosuccinates, polyoxyalkylene fatty acid amide ether sulfuric acids, monoglyceride sulfuric acids, α-olefinsulfonic acids, acylated isethionic acids, alkyl glyceryl ether sulfonic acids, acylated glutamic acids and alkanesulfonic acids, as well as salts thereof. Specific examples thereof include those represented by the following (B-1) to (B-8).

(B-1) Alkyl sulfosuccinates, polyoxyalkylene alkyl ether sulfosuccinates or salts thereof represented by the general formula (4):

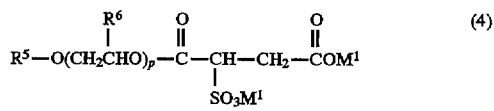

wherein $M^1$ is a hydrogen atom, alkali metal, alkaline earth metal, ammonium or alkanolamine, $R^5$ is a linear or branched alkyl or alkenyl group having 8–24 carbon atoms, $R^6$ radicals to the number of p may be indential with or different from each other and are independently a hydrogen atom or a methyl group, and p is a number of 0–20.

(B-2) Polyoxyalkylene fatty acid amide ether sulfuric acids or salts thereof represented by the general formula (5):

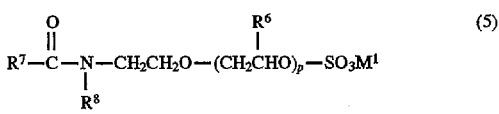

wherein $R^6$, $M^1$ and p have the same meaning as defined above, $R^7$ is a linear or branched alkyl or alkenyl group having 7–23 carbon atoms, and $R^8$ is a hydrogen atom or an alkyl group having 1–5 carbon atoms.

(B-3) Monoglyceride sulfuric acids having a linear or branched, saturated or unsaturated fatty acid group having 8–24 carbon atoms, or their salts with an alkali metal, alkaline earth metal, ammonium or alkanolamine.

(B-4) α-Olefinsulfonic acids obtained by sulfonating a linear or branched α-olefin having 8–24 carbon atoms, or their salts with an alkali metal, alkaline earth metal, ammonium or alkanolamine.

(B-5) Acylated isethionic acids having a linear or branched, saturated or unsaturated acyl group having 8–24 carbon atoms, or their salts with an alkali metal, alkaline earth metal, ammonium or alkanolamine.

(B-6) Alkyl glyceryl ether sulfonic acids having a linear or branched alkyl or alkenyl group having 8–24 carbon atoms or an alkylene oxide adduct thereof, or their salts with an alkali metal, alkaline earth metal, ammonium or alkanolamine.

(B-7) Acylated glutamic acids having a linear or branched, saturated or unsaturated acyl group having 8–24 carbon atoms, or their salts with an alkali metal, alkaline earth metal, ammonium or alkanolamine.

(B-8) Primary or secondary alkanesulfonic acids having a linear or branched, saturated or unsaturated alkyl or alkenyl group having 8–24 carbon atoms, or their salts with an alkali metal, alkaline earth metal, ammonium or alkanolamine.

Among these components (B), the alkyl sulfosuccinates, polyoxyalkylene alkyl ether sulfosuccinates, polyoxyalkylene fatty acid amide ether sulfuric acids, monoglyceride sulfuric acids, α-olefinsulfonic acids, acylated glutamic acids or salts thereof are preferred.

These components (B) may be used either singly or in any combination thereof. No particular limitation is imposed on the amount of the component (B) to be incorporated into the detergent composition according to the present invention. However, it is preferably incorporated in a proportion of 0.1–45 wt. % particularly 0.1–30 wt. %, most preferably 0.5–20 wt. %. If the proportion of the component (B) to be blended is lower than 0.1 wt. %, the resulting detergent composition fails to produce creamy foams. On the other hand, any proportion exceeding 45 wt. % results in a detergent composition deteriorated in foamability. It is hence not preferable to blend the component (B) in any proportion outside the above range.

No particular limitation is imposed on the blending ratio of the component (A) to the component (B) in the detergent composition according to the present invention. However, it is preferred from the viewpoint of foamability that the component (A) be incorporated in an amount more than the component (B).

It is also preferred that the detergent composition according to the present invention be adjusted to pH 2–10, more preferably 4–8, most preferably 4–7 with any known acidic or basic substance used in the conventional detergent compositions (conditions for pH measurement: aqueous solution containing 5 wt. % of active ingredients)

In the detergent compositions according to the present invention, it is possible to incorporate as needed, in addition to the above-described essential components, various components such as anionic surfactants other than the components (A) and (B), nonionic surfactants, cationic surfactants and conditioning components within limits not impeding the effects of the present invention.

Examples of such anionic surfactants include fatty acid salts, polyoxyalkylene alkyl ether acetates, alkylsulfates, polyoxyalkylene alkyl ether sulfates, sulfosuccinamate type surfactants, alkylphosphates and polyoxyalkylene alkyl ether phosphates. Examples of the nonionic surfactants include alkyl polyglucosides, sucrose fatty acid esters, polyglycerol fatty acid esters, polyoxyalkylene alkyl ethers, fatty acid alkanolamides, alkylamine oxides and polyhydric alcohol esters of fatty acids. Examples of the cationic surfactants include mono- or di-long-chain, linear or branched alkyl quaternary ammonium salts and mono- or di-long-chain, linear or branched alkyl tertiary amines. Examples of the conditioning components include oily substances such as higher alcohols, silicone, silicone derivatives, lanolin, squalene, hydrocarbons, protein derivatives and polyethylene glycol fatty acid esters, and cationized polymers such as cationized cellulose, cationized guar gum, Merquat 550 (product of Merck & Co., Inc.) and Merquat 100 (product of Merck & Co., Inc.).

Besides the essential components described above, other components routinely employed in detergent composition, for example, water-soluble polymers such as methylcellulose, hydroxyethylcellulose, carboxyvinyl polymers and polysaccharides such as xanthan gum; viscosity modifiers such as polyoxyalkylene sorbitan esters, polyoxyethylene glycol distearate and ethanol; chelating agents such as ethylenediaminetetraacetic acid (EDTA) and phosphonic acid salts; antiseptics such as methylparaben and butylparaben; nutritive components such as vitamins and precursors thereof; animal and vegetable extracts such as lecithin and gelatin, or derivatives thereof; fine powders of polymers such as nylon and polyethylene; antiphlogistics such as dipotassium glycyrrhetinate; disinfectants and antidandruff agents such as triclosan, triclocarban, Octopirox and zinc pyrithione; antioxidants such as dibutylhydroxytoluene; and others such as pearly luster-imparting agents, ultraviolet absorbents, pH adjustors, coloring matter and perfume bases may be incorporated as needed within limits not impeding the effects of the present invention.

The detergent compositions according to the present invention can be used as skin and hair detergents, and besides, detergents intended for various applications, for example, dishwashing detergents, laundry detergents and foam bath. In this case, the total amount of the surfactants including the component (A), the component (B) and other surfactants to be incorporated in the composition is preferably controlled to at least 30 wt. % for a solid form, at least 20 wt. % for a paste form or at least 10 wt. % for a liquid form.

EXAMPLES

The present invention will hereinafter be described more specifically by the following examples. However, the present invention is not limited to these examples.

Synthetic Example 1

Synthesis of an Amide-ether Carboxylic Acid Salt Containing an Amide-ether

Into a product obtained by heating 214.4 g (1 mol) of methyl laurate, 61.7 g (1.02 mol) of monoethanolamine and 15.3 g of a 30 wt. % methanol solution of sodium methoxide for 5 hours at 90° C. under 50 mmHg, 88.2 g (2 mol) of ethylene oxide were introduced at 100°–110° C. under a gauge pressure of 0–3.5 atm.

The thus-obtained reaction mixture in an amount of 331 g was heated to 70°–75° C., to which 174.8 g (1.5 mol) of sodium monochloroacetate (SMCA) and 65.2 g of solid sodium hydroxide were added over 4 hours. SMCA and sodium hydroxide were divided into 5 portions and added at the beginning of the reaction, and after 1 hour, 2 hours, 3 hours and 4 hours from the beginning of the reaction. After the fourth-hour addition, the reaction mixture was aged for 1 hour. The reaction temperature was then raised to 85° C., and 5.3 g of water were added, followed by aging further for 1 hour, thereby obtaining 592 g of a reaction mixture. Add to this reaction mixture were 500 g of water, and 36% hydrochloric acid was added at 90° C. to adjust the pH of the reaction mixture to 2.8. After stirring the reaction mixture for 1 hour, it was left at rest for 1 hour to conduct separation between layers, thereby obtaining 545 of a product in an acid form. This compound in the acid form was neutralized with 30% aqueous sodium hydroxide to pH 7, and water was added to prepare a transparent solution, thereby obtaining an amide-ether derivative mixture 2 shown in Table 1.

Synthetic Examples 2–6

Syntheses of Amide-ether Carboxylic Acid Salts Separately Containing an Amide-ether Amide-ether derivative mixtures 1, 3, 5 and 6 shown in Table 1 were obtained in a manner similar to Synthetic Example 1. Incidentally, the molar ratios of sodium monochloroacetate acid to the amide-ether were changed to 1.7, 1.5, 1.5 and 1.4, respectively, and the molar ratios of the solid sodium hydroxide to the amide-ether were changed to 1.85, 1.63, 1.63 and 1.52, respectively. Besides, an amide-ether derivative mixture 4 was obtained in the same manner as in Synthetic Example 1 except that the conversion to the acid form and its purification were not performed, but after the reaction, the reaction mixture was neutralized with 30% aqueous sodium hydroxide to pH 7 as it is.

Synthetic Example 7

Synthesis of an Amide-ether Carboxylic Acid Salt Containing an Amide-ether

The product in the acid form obtained in Synthetic Example 1 was neutralized with a 30% aqueous suspension of magnesium hydroxide to pH 6–7, and water was added to prepare a transparent solution, thereby obtaining an amide-ether derivative mixture 7 shown in Table 1.

Comparative Synthetic Example 1

Synthesis of an Amide-ether Carboxylic Acid Salt Containing Glycerol Derivatives Into a product obtained by melting 510.6 g (2.2 mol) of purified coconut oil at 35° C. and then heating the melt together with 138.8 g (2.3 mol) of monoethanolamine and 5.1 g of a 30 wt. % methanol solution of sodium methoxide for 2 hours at 70° C. and 6 hours at 105° C., 298 g (6.75 mol) of ethylene oxide were introduced over 30 minutes at 100°–110° C. under a gauge pressure of 0–3.5 atm.

The thus-obtained reaction mixture in an amount of 675 g was heated to 70°–75° C., to which 281.7 g (2.41 mol) of SMCA and 105.1 g of solid sodium hydroxide were added over 4 hours. SMCA and sodium hydroxide were divided into 5 portions and added at the beginning of the reaction, and after 1 hour, 2 hours, 3 hours and 4 hours from the beginning of the reaction. After the fourth-hour addition, the reaction mixture was aged for 1 hour. The reaction temperature was then raised to 85° C., and 5 g of water were added, followed by aging further for 1 hour, thereby obtaining 1039 g of a reaction mixture. Add to this reaction mixture were 500 g of water, and 36% hydrochloric acid was added at 50° C. to adjust the pH of the reaction mixture to 7. The reaction mixture was diluted with water to a transparent solution, thereby obtaining an amide-ether derivative mixture 10 shown in Table 1.

Comparative Synthetic Example 2

Synthesis of the Sodium Salt of an Amide-ether Carboxylic Acid, from which an Amide-ether is Removed After carboxymethylation was conducted in the same manner as in Synthetic Example 1 to obtain a reaction mixture, ethanol was added to this reaction mixture to deposit solids. The solids were then collected by filtration and added with ethanol to wash them, thereby removing an amide-ether. The residue was then treated in the same manner as in Synthetic Example 1 to obtain a product in an acid form. The product was then neutralized with 30% aqueous sodium hydroxide to obtain an amide-ether derivative mixture 8 shown in Table 1.

Comparative Synthetic Example 3

Synthesis of the Sodium Salt of an Amide-ether Carboxylic Acid Containing an Amide-ether An amide-ether was obtained in the same manner as in Synthetic Example 1, and this amide-ether was further reacted under conditions that molar ratios of SMCA and solid sodium hydroxide to the amide-ether were each 0.05. Thereafter, the reaction mixture was treated in the same manner as in Synthetic Example 1 to obtain an amide-ether derivative 9 shown in Table 1.

TABLE 1

| | | | Content in solids (wt. %) | | | | | |
|---|---|---|---|---|---|---|---|---|
| Sample | Compound (1) | Compound (2) | (1) | (2) | (1) + (2) | (3) | Other* | (1): (2) |
| Amide-ether derivative mixture 1 | $R^1$: $C_{11}H_{23}$<br>$R^2$: H<br>M: Na<br>n: 1 | $R^1$: $C_{11}H_{23}$<br>$R^3$: H<br>n: 1 | 91 | 7 | 98 | 0 | 2 | 93:7 |
| Amide-ether | $R^1$: $C_{11}H_{23}$ | $R^1$: $C_{11}H_{23}$ | 82 | 14 | 96 | 0 | 4 | 85:15 |

TABLE 1-continued

| Sample | Compound (1) | Compound (2) | Content in solids (wt. %) | | | | | (1):(2) |
|---|---|---|---|---|---|---|---|---|
| | | | (1) | (2) | (1)+(2) | (3) | Other* | |
| derivative mixture 2 | $R^2$: H<br>M: Na<br>n: 3 | $R^3$: H<br><br>n: 3 | | | | | | |
| Amide-ether derivative mixture 3 | $R^1$: $C_{11}H_{23}$<br>$R^2$: H<br>M: Na<br>n: 5 | $R^1$: $C_{11}H_{23}$<br>$R^3$: H<br><br>n: 5 | 77 | 18 | 95 | 0 | 5 | 81:19 |
| Amide-ether derivative mixture 4 | $R^1$: $C_{11}H_{23}$<br>$R^2$: H<br>M: Na<br>n: 3 | $R^1$: $C_{11}H_{23}$<br>$R^3$: H<br><br>n: 3 | 49 | 12 | 61 | 0 | 39 | 80:20 |
| Amide-ether derivative mixture 5 | $R^1$: $C_{13}H_{27}$<br>$R^2$: H<br>M: Na<br>n: 6 | $R^1$: $C_{13}H_{27}$<br>$R^3$: H<br><br>n: 6 | 70 | 23 | 93 | 0 | 7 | 75:25 |
| Amide-ether derivative mixture 6 | $R^1$: $C_{17}H_{35}$<br>$R^2$: H<br>M: Na<br>n: 10 | $R^1$: $C_{17}H_{35}$<br>$R^3$: H<br><br>n: 10 | 60 | 35 | 95 | 0 | 5 | 63:37 |
| Amide-ether derivative mixture 7 | $R^1$: $C_{11}H_{23}$<br>R: H<br>M: Mg<br>n: 3 | $R^1$: $C_{11}H_{23}$<br>$R^3$: H<br><br>n: 3 | 82 | 14 | 96 | 0 | 4 | 85:15 |
| Amide-ether derivative mixture 8 | $R^1$: $C_{11}H_{23}$<br>$R^2$: H<br>M: Na<br>n: 3 | $R^1$: $C_{11}H_{23}$<br>$R^3$: H<br><br>n: 3 | 96 | 1> | 96 | 0 | 4 | 100:0 |
| Amide-ether derivative mixture 9 | $R^1$: $C_{11}H_{23}$<br>$R^2$: H<br>M:<br>n: 4 | $R^1$: $C_{11}H_{23}$<br>$R^3$: H<br>Na<br>n: 4 | 4 | 90 | 94 | 0 | 6 | 4:96 |
| Amide-ether derivative mixture 10 | $R^1$: $C_{11}H_{23}$—$C_{13}H_{27}$<br>R: H<br>M: Na<br>n: 3 | $R^1$: $C_{11}H_{23}$—$C_{13}H_{27}$<br>R: H<br><br>n: 3 | 23 | 25 | 48 | 30 | 22 | 48:52 |

*: Sodium chloride, glycolic acid salts, etc.

Example 1

Detergent compositions having their corresponding formulations shown in Table 2 were prepared and individually evaluated as to volume of foams formed, quality of foams and irritativeness to the skin. The results are shown in Table 2.

Incidentally, blending amounts, wt. %, shown in Table 2 are values as to actual contents of surfactants (solids content for the amide-ether carboxylic acid salts). The adjustment of pH was conducted with aqueous sodium hydroxide and citric acid.

<Evaluation Methods>

One gram of each detergent sample was applied to 20 g (15 cm long) of the hair of a healthy Japanese woman and foamed for 1 minutes, and the volume of foams formed and quality of foams were observed by 20 expert panelists and ranked in accordance with the following respective evaluation standards. The results are shown in table 2 in terms of an average score of the 20 panelists in accordance with the following criterion.

The irritativeness to the skin was evaluated in the following manner. Each sample of the detergent compositions was applied 4 times to the healthy skins of guinea pigs (5 heads per sample). After the fourth application, the condition of the skin reaction of each group of guinea pigs was observed and ranked in accordance with the following evaluation standard. The results are shown in table 2 in terms of an average score of the 5 guinea pigs in accordance with the following criterion.

<Standards and Criteria>

(1) Volume of foams formed:
  A. Ranking:
    Very good foaming . . . Score 4
    Good foaming . . . Score 3
    Somewhat insufficient foaming . . . Score 2
    Inferior foaming . . . Score 1
  B. Criterion:
    Average score 3.5–4.0 . . . ⊚
    Average score 2.5–3.4 . . . ○
    Average score 1.5–2.4 . . . Δ
    Average score 1.0–1.4 . . . x
(2) Quality of Foams:
  A. Ranking:
    Foam quality was creamy and very smooth . . . Score 4
    Foam quality was creamy and smooth . . . Score 3
    Foam quality was somewhat coarse and rough . . . Score 2
    Foam quality was coarse and rough . . . Score 1
  B. Criterion:
    Average score 3.5–4.0 . . . ⊚
    Average score 2.5–3.4 . . . ○
    Average score 1.5–2.4 . . . Δ

Average score 1.0–1.4 . . . x (3) Irritativeness to the skin:
  A. Ranking:
   Unirritative (no reaction was observed) . . . Score 5
   Faintly irritative (slight erythema was observed) . . . Score 4
   Weakly irritative (clear erythema was observed) . . . Score 3
   Fairly irritative (clear erythema was accompanied by edema) . . . Score 2
   Strongly irritative (clear erythema was accompanied by necrosis or asphyxia) . . . Score 1
  B. Criterion:
   Average score 3.5–5.0 . . . ○
   Average score 2.5–3.4 . . . Δ
   Average score 1.0–2.4 . . . x

TABLE 2

|  | Invention product | | | | Comparative product | | | | | |
| --- | --- | --- | --- | --- | --- | --- | --- | --- | --- | --- |
|  | 1 | 2 | 3 | 4 | 1 | 2 | 3 | 4 | 5 | 6 |
| Amide-ether derivative mixture 1 | 10 | — | 10 | — | — | — | — | — | — | — |
| Amide-ether derivative mixture 2 | — | 10 | — | — | 10 | — | — | — | — | — |
| Amide-ether derivative mixture 7 | — | — | — | 10 | — | — | — | — | — | — |
| Amide-ether derivative mixture 8 | — | — | — | — | — | 10 | — | — | 10 | — |
| Amide-ether derivative mixture 9 | — | — | — | — | — | — | 10 | — | — | — |
| Amide-ether derivative mixture 10 | — | — | — | — | — | — | — | 10 | — | 20 |
| Disodium polyoxyethylene (3) lauryl ether sulfosuccinate | 4 | — | — | — | — | — | 2 | — | — | 4 |
| Sodium α-olefin-*1 sulfonate | — | 5 | — | 4 | — | — | — | 6 | — | — |
| Triethanolamine lauroylglutmate | — | — | 3 | — | — | — | — | — | 2 | — |
| Deionized water | Balance | | | | | | | | | |
| pH (5% aqueous solution of active ingredient) | 6.5 | 5.2 | 6.1 | 6.5 | 5.6 | 6.8 | 6.4 | 5.9 | 6.4 | 6.4 |
| Evaluation | | | | | | | | | | |
| Volume of foams formed | ⊚ | ⊚ | ⊚ | ⊚ | ○ | X | X | X | Δ | X |
| Quality of foams | ⊚ | ⊚ | ⊚ | ⊚ | Δ | Δ | X | X | Δ | X |
| Irritativeness to the skin | ○ | ○ | ○ | ○ | X | ○ | ○ | ○ | ○ | ○ |

*1: Obtained by sulfonating Dialene 124 (product of Mitsubishi Chemical Industries Limited), followed by neutralization.

Example 2

A shampoo having the following composition and a pH of 6.7 was prepared. This shampoo was low in irritativeness to the skin and excellent in foamability and quality of foams.

|  | (wt. %) |
| --- | --- |
| Amide-ether derivative mixture 3 | 14 |
| Sodium coconut oil fatty acid isethionate | 3 |
| Diethanolamide laurate | 3 |
| Perfume base | 0.2 |
| Citric acid | q.s. |
| Sodium hydroxide | q.s. |
| Deionized water | Balance |

Example 3

A body shampoo having the following composition and a pH of 6.1 was prepared. This body shampoo was low in irritativeness to the skin and excellent in foamability and quality of foams.

|  | (wt. %) |
| --- | --- |
| Amide-ether derivative mixture 6 | 10 |
| Sodium coconut oil fatty acid monoethanolamide polyoxyethylene ether sulfate (Sanamide C-3, product of Nippon Oil & Fats Co., Ltd.) | 7 |
| Perfume base | 0.2 |
| Citric acid | q.s. |
| Sodium hydroxide | q.s. |
| Deionized water | Balance |

Example 4

A shampoo having the following composition and a pH of 4.6 was prepared. This shampoo was low in irritativeness to the skin and excellent in foamability and quality of foams.

|  | (wt. %) |
| --- | --- |
| Amide-ether derivative mixture 4 | 10 |
| Disodium polyoxyethylene (7) alkyl ether sulfosuccinate (Softanol MES7H, product of Nippon Shokubai Kagaku Kogyo Co., Ltd.) | 5 |
| Monoethanolamide laurate | 2 |
| Perfume base | 0.2 |
| Citric acid | q.s. |
| Sodium hydroxide | q.s. |
| Deionized water | Balance |

Example 5

A shampoo having the following composition and a pH of 6.9 was prepared. This shampoo was low in irritativeness to the skin and excellent in foamability and quality of foams.

|  | (wt. %) |
| --- | --- |
| Amide-ether derivative mixture 4 | 10 |
| Sodium α-olefinsulfonate [obtained by sulfonating Dialene 124 (product of Mitsubishi Chemical Industries Limited), followed by neutralization] | 4 |
| Ammonium lauryl sulfate | 3 |
| Laurylamine oxide | 2 |
| Perfume base | 0.2 |
| Citric acid | q.s. |
| Sodium hydroxide | q.s. |
| Deionized water | Balance |

Example 6

A dishwashing detergent having the following composition and a pH of 6.4 was prepared. This dishwashing detergent was low in irritativeness to the skin and excellent in detergency, foamability, quality of foams and hand feel after washing.

|  | (wt. %) |
|---|---|
| Amide-ether derivative mixture 1 | 15 |
| Sodium lauryl glyceryl ether sulfonate | 5 |
| Ethanol | 2 |
| Perfume base | 0.2 |
| Citric acid | q.s. |
| Sodium hydroxide | q.s. |
| Deionized water | Balance |

Example 7

A conditioning shampoo having the following composition and a pH of 6.1 was prepared. This conditioning shampoo was low in irritativeness to the skin and excellent in foamability, quality of foams and feel upon shampooing and rinsing.

|  | (wt. %) |
|---|---|
| Amide-ether derivative mixture 3 | 8 |
| Amide-ether derivative mixture 7 | 5 |
| Disodium polyoxyethylene (3) lauryl ether sulfosuccinate | 4 |
| Dodecyl polyglucoside | 2 |
| Hydrolyzed collagen | 0.5 |
| Cationized guar gum (Jaguar C-13-S, product of Celanese Schtein Hall Co.). | 0.4 |
| Dimethyl polysiloxane (2,000,000 cS) | 0.2 |
| Monostearyltrimethylammonium chloride | 0.2 |
| Propylene glycol | 2 |
| Perfume base | 0.2 |
| Citric acid | q.s. |
| Sodium hydroxide | q.s. |
| Deionized water | Balance |

Example 8

A body shampoo having the following composition and a pH of 7.0 was prepared. This body shampoo was low in irritativeness to the skin and excellent in foamability and quality of foams.

|  | (wt. %) |
|---|---|
| Amide-ether derivative mixture 2 | 3 |
| Amide-ether derivative mixture 7 | 5 |
| Sodium α-olefinsulfonate [obtained by sulfonating Dialene 124 (product of Mitsubishi Chemical Industries Limited), followed by neutralization] | 3 |
| Dodecyl polyglucoside | 3 |
| Propylene glycol | 2 |
| Perfume base | 0.4 |
| Citric acid | q.s. |
| Sodium hydroxide | q.s. |
| Deionized water | Balance |

Example 9

A dishwashing detergent having the following composition and a pH of 6.9 was prepared. This dishwashing detergent was low in irritativeness to the skin and excellent in detergency, foamability, quality of foams and hand feel after washing.

|  | (wt. %) |
|---|---|
| Amide-ether derivative mixture 4 | 7 |
| Sodium monoglyceride sulfate [obtained by sulfating coconut oil fatty acid monoglyceride, followed by neutralization] | 4 |
| Disodium polyoxyethylene (3) lauryl ether sulfosuccinate | 4 |
| Lauryldimethylamine oxide | 3 |
| Dodecyl polyglucoside | 2 |
| Ethanol | 2 |
| Magnesium chloride | 0.3 |
| Perfume base | 0.2 |
| Citric acid | q.s. |
| Sodium hydroxide | q.s. |
| Deionized water | Balance |

Example 10

A dishwashing detergent having the following composition and a pH of 6.9 was prepared. This dishwashing detergent was low in irritativeness to the skin and excellent in detergency, foamability, quality of foams and hand feel after washing.

|  | (wt. %) |
|---|---|
| Amide-ether derivative mixture 3 | 8 |
| Sodium alkanesulfonate [Hostapur SAS60, product of Hoechst AG] | 5 |
| Sodium polyoxyethylene (3) lauryl ether sulfate | 4 |
| Magnesium chloride | 0.05 |
| Ethanol | 3 |
| Perfume base | 0.1 |
| Citric acid | q.s. |
| Sodium hydroxide | q.s. |
| Deionized water | Balance |

INDUSTRIAL APPLICABILITY

The detergent compositions according to the present invention have low irritativeness to the skin and the like and excellent foamability, and produce creamy foams, and are hence useful as skin and hair detergents, and besides, dishwashing detergents, laundry detergents, detergents for bathroom, etc.

We claim:

1. A detergent composition comprising the following components (A) and (B):

(A) an amide-ether derivative mixture comprising an amide-ether carboxylic acid or a salt thereof represented by the following general formula (1) and an amide-ether represented by the following general formula (2) in a weight ratio (1)/(2) of 95:5 to 60:40 in a proportion of at least 50 wt. % in total based on solids in the component (A), and containing glycerol derivatives represented by the following general formula (3) in a proportion not higher than 5 wt. % of the solids:

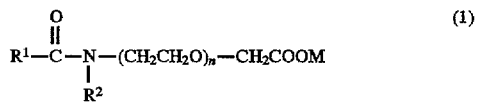

-continued

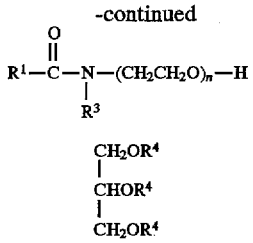

$$R^1-\overset{\overset{O}{\|}}{C}-\underset{\underset{R^3}{|}}{N}-(CH_2CH_2O)_n-H \quad (2)$$

$$\begin{array}{l} CH_2OR^4 \\ | \\ CHOR^4 \\ | \\ CH_2OR^4 \end{array} \quad (3)$$

wherein $R^1$ is a linear or branched alkyl or alkenyl group having 7–17 carbon atoms, or a phenyl group substituted by an alkyl group having 7–17 carbon atoms, $R^2$ is a hydrogen atom or an alkyl group having 1–3 carbon atoms, M is a hydrogen atom, alkali metal, alkaline earth metal, ammonium, alkanolamine or basic amino acid, $R^3$ is a hydrogen atom or an alkyl group having 1–3 carbon atoms, and $R^4$ is a hydrogen atoms, $-(CH_2CH_2O)_nCH_2COOM$ or $-(CH_2CH_2O)_mH$, n and m are independently a number of from 1 to 10 with the proviso that respective $R^1$, M, n and m in the general formulae (1), (2) and (3) may be identical with or different from one another; and (B) an anionic surfactant selected from the group consisting of alkyl sulfosuccinates, polyoxyalkylene alkyl ether sulfosuccinates, polyoxyalkylene fatty acid amide ether sulfuric acids, monoglyceride sulfuric acids, α-olefinsulfonic acids, acylated isethionic acids, alkyl glyceryl ether sulfonic acids, and salts thereof, wherein the content of the component (A) is 3–30 wt. % and the content of the component (B) is 0.1–30 wt. %.

2. The detergent composition according to claim 1, wherein the component (A) is an amide-ether derivative mixture comprising the amide-ether carboxylic acid or the salt thereof represented by the general formula (1) and the amide-ether represented by the general formula (2) in a weight ratio (1)/(2) of 95:5 to 60:40 in a proportion of at least 60 wt. % in total of the solids, and containing the glycerol derivatives represented by the general formula (3) in a proportion not higher than 3 wt. % of the solids.

3. The detergent composition according to claim 2, wherein the component (A) is an amide-ether derivative mixture which does not contain substantially the glycerol derivatives represented by the general formula (3).

4. The detergent composition according to claim 1, wherein the component (A) is obtained by using, as a raw material, a fatty acid alkanolamide synthesized from a lower alcohol ester of a fatty acid.

5. The detergent composition according to claim 1, which has a pH of 4–7.

* * * * *

UNITED STATES PATENT AND TRADEMARK OFFICE
CERTIFICATE OF CORRECTION

PATENT NO. : 5,693,605
DATED : DECEMBER 2, 1997
INVENTOR(S) : ISOBE, ET AL.

It is certified that error appears in the above-identified patent and that said Letters Patent is hereby corrected as shown below:

On the Title Page, Column 1, "[22] Filed: Apr. 10, 1996"

should read --[22] PCT Filed: Aug. 7, 1995--.

On the Title Page, Column 1, please insert the following:

--[86]  PCT No.:        PCT/JP95/01566

§ 371 Date:      Apr. 10, 1996

§ 102(e) Date:   Apr. 10, 1996--.

Signed and Sealed this

Fifteenth Day of December, 1998

Attest:

BRUCE LEHMAN

*Attesting Officer*        *Commissioner of Patents and Trademarks*